(12) United States Patent
Bar-Tal

(10) Patent No.: US 11,751,936 B2
(45) Date of Patent: Sep. 12, 2023

(54) CONFIGURING PERIMETER OF BALLOON ELECTRODE AS LOCATION SENSOR

(71) Applicant: Biosense Webster (Israel) Ltd., Yokneam (IL)

(72) Inventor: Meir Bar-Tal, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 640 days.

(21) Appl. No.: 16/198,487

(22) Filed: Nov. 21, 2018

(65) Prior Publication Data

US 2020/0155224 A1 May 21, 2020

(51) Int. Cl.
*A61B 18/14* (2006.01)
*A61B 18/00* (2006.01)
*A61B 34/20* (2016.01)

(52) U.S. Cl.
CPC .. *A61B 18/1492* (2013.01); *A61B 2018/0022* (2013.01); *A61B 2018/00077* (2013.01); *A61B 2018/00351* (2013.01); *A61B 2018/00375* (2013.01); *A61B 2018/00577* (2013.01); *A61B 2018/00773* (2013.01); *A61B 2018/00839* (2013.01); *A61B 2034/2046* (2016.02)

(58) Field of Classification Search
CPC ...... A61B 18/1492; A61B 2018/00077; A61B 2018/0022; A61B 2018/00351; A61B 2018/00375; A61B 2018/00577; A61B 2018/00773; A61B 2018/00839; A61B 2017/00243; A61B 2017/00557; A61B 2017/00526; A61B 34/20; A61B 2034/2051
See application file for complete search history.

(56) References Cited

U.S. PATENT DOCUMENTS

| 5,391,199 A | 2/1995 | Ben-Haim |
| 6,239,724 B1 | 5/2001 | Doron et al. |
| 6,332,089 B1 | 12/2001 | Acker et al. |
| 6,484,118 B1 | 11/2002 | Govari |
| 6,574,492 B1 | 6/2003 | Ben-Haim et al. |
| 6,618,612 B1 | 9/2003 | Acker et al. |
| 6,690,963 B2 | 2/2004 | Ben-Haim et al. |

(Continued)

FOREIGN PATENT DOCUMENTS

| CN | 105960261 A | 9/2016 |
| EP | 1 820 464 A1 | 8/2007 |

(Continued)

OTHER PUBLICATIONS

International Search Report and Written Opinion dated Apr. 28, 2020 in International Application No. PCT/IBZ019/059657, 14 pages.

*Primary Examiner* — Linda C Dvorak
*Assistant Examiner* — Lindsay Regan Lancaster
(74) *Attorney, Agent, or Firm* — Lewis Roca Rothgerber Christie LLP

(57) ABSTRACT

An expandable balloon, which is coupled to a distal end of a shaft for insertion into an organ of a patient, includes an expandable membrane, one or more electrodes and one or more respective conductive coils. The one or more electrodes are disposed over an external surface of the membrane. The one or more respective conductive coils are each disposed proximate a respective RF ablation electrode. The one or more conductive coils are configured as magnetic sensors.

23 Claims, 4 Drawing Sheets

(56) References Cited

U.S. PATENT DOCUMENTS

| | | | |
|---|---|---|---|
| 8,998,893 B2* | 4/2015 | Avitall | A61B 18/1492 |
| | | | 606/41 |
| 2002/0065455 A1 | 5/2002 | Ben-Haim et al. | |
| 2002/0087156 A1 | 7/2002 | Maguire et al. | |
| 2003/0120150 A1 | 6/2003 | Govari | |
| 2004/0068178 A1 | 4/2004 | Govari | |
| 2012/0136418 A1* | 5/2012 | Buckley | A61B 18/02 |
| | | | 607/105 |
| 2012/0197109 A1* | 8/2012 | Hartmann | A61B 34/20 |
| | | | 600/424 |
| 2014/0364848 A1 | 12/2014 | Heimbecher et al. | |
| 2016/0029998 A1* | 2/2016 | Brister | A61B 8/56 |
| | | | 600/424 |
| 2017/0312022 A1* | 11/2017 | Beeckler | A61B 18/1492 |
| 2018/0228392 A1* | 8/2018 | Govari | A61B 5/6852 |
| 2018/0344202 A1* | 12/2018 | Bar-Tal | A61B 90/39 |

FOREIGN PATENT DOCUMENTS

| | | | | |
|---|---|---|---|---|
| EP | 2 875 790 A2 | 5/2015 | | |
| WO | WO 96/05768 A1 | 2/1996 | | |
| WO | WO 00/10456 A1 | 3/2000 | | |
| WO | WO-2015085011 A1 * | 6/2015 | | A61B 5/14539 |
| WO | WO-2016154494 A2 * | 9/2016 | | H01L 25/112 |
| WO | WO 2018/220479 A1 | 12/2018 | | |

* cited by examiner

CONFIGURING PERIMETER OF BALLOON ELECTRODE AS LOCATION SENSOR

FIELD OF THE INVENTION

The present invention relates generally to tracking a probe within a living body, and specifically to magnetic-based measurements.

BACKGROUND OF THE INVENTION

Intrabody probes, such as catheters, may include position sensors at their distal ends. For example, U.S. Patent Application Publication 2002/0087156 describes a method for attaching a sensor to an inflatable balloon. The method is particularly useful in the construction of a tissue ablation catheter for forming a lesion along a substantially circumferential region of tissue wherein a sensor is used for monitoring the temperature of the tissue being ablated. In an embodiment, one or more position sensor elements (not shown) are located in, or near, the expandable member. A circumferential ablation member with the ablation element that forms an ablative circumferential band that circumscribes an expandable member embodied as a balloon. In a sequential mode of operation for the ablation member, the position sensor of the position monitoring assembly may be coupled to the expandable member.

As another example, U.S. Pat. No. 6,574,492 describes a catheter for measuring physiological signals in a heart comprises a structure at a distal end of the catheter wherein the structure has a plurality of arms, an electrode fixed to each arm and a device for generating position information located on each arm. The arms are located near the long axis of the catheter during insertion of the catheter within a heart and the arms are spreadable apart and away from the long axis of the catheter when the structure is within the heart. In a preferred embodiment of the invention, a position sensor having one or more coils is embedded in a lobe, preferably near an electrical sensor, so as to more exactly determine the relative position of the electrical sensor.

U.S. Patent Application Publication 2014/0364848 describes a system for diagnosis or treatment of tissue in a body. The system includes an ablation catheter having an ablation delivery member disposed proximate a distal end of a shaft of the catheter and configured to deliver ablation energy to ablate the tissue. In one embodiment, the ablation delivery member comprises an ablation electrode and may also be configured to generate a signal indicative of electrical activity in the tissue. The catheter further includes one or more sensing electrodes disposed proximate the ablation delivery member. The sensing electrodes are configured to generate signals indicative of electrical activity in the tissue. In an embodiment, the sensing electrodes function as position sensors.

SUMMARY OF THE INVENTION

An embodiment of the present invention provides an expandable balloon coupled to a distal end of a shaft for insertion into an organ of a patient. The expandable balloon includes an expandable membrane, one or more electrodes and one or more respective conductive coils. The one or more electrodes are disposed over an external surface of the membrane. The one or more respective conductive coils are each disposed proximate a respective RF ablation electrode. The one or more conductive coils are configured as magnetic sensors.

In some embodiments, the expandable balloon further includes one or more respective leads, each configured to provide a common electrical contact for an electrode and for a coil wound around the electrode.

In some embodiments, the conductive coil is disposed on a flexible printed board (PBC), and wherein the flexible PCB is attached to the expandable membrane.

In an embodiment, the one or more electrodes are radiofrequency (RF) ablation electrodes. In an alternative embodiment, the one or more electrodes are sensing electrodes to sense signals produced by cardiac tissues.

There is additionally provided, in accordance with an embodiment of the present invention, a system including an expandable balloon and a processor. The expandable balloon is coupled to a distal end of a shaft for insertion into an organ of a patient, wherein the expandable balloon includes an expandable membrane, one or more electrodes, and one or more respective conductive coils. The one or more electrodes are disposed over an external surface of the membrane. The one or more respective conductive coils are each disposed proximate a respective RF ablation electrode, wherein the one or more conductive coils are configured as magnetic sensors. The processor is configured to, based on signals received from the one or more conductive coils, estimate a spatial configuration of the expandable balloon inside the organ.

In some embodiments, the processor is configured to estimate the spatial configuration of the expandable balloon by estimating a location of the balloon inside the organ.

In some embodiments, the processor is configured to estimate the spatial configuration of the expandable balloon by estimating an orientation of the balloon inside the organ.

In an embodiment, the processor is configured to estimate the orientation by estimating at least one of a deflection of the balloon relative to a longitudinal axis defined by the distal end of the shaft and a roll angle about the longitudinal axis.

In another embodiment, the processor is configured to estimate the spatial configuration of the expandable balloon by estimating a shape of the balloon inside the organ.

In some embodiments, the processor is configured to estimate the shape by identifying an extent of expansion of the balloon.

In an embodiment, the processor is configured to estimate the shape by detecting whether the balloon is fully expanded or not.

There is further provided, in accordance with an embodiment of the present invention, a method, including irradiating one or more magnetic fields in a body of a patient. Signals resulting from the generated magnetic fields are generated by one or more conductive coils that are disposed proximate each electrode disposed over an external surface of a membrane of an expandable balloon coupled to a distal end of a shaft inserted in an organ of the patient. Based on the generated signals, a spatial configuration of the expandable balloon inside the organ is estimated using a magnetic tracking system.

There is furthermore provided, in accordance with an embodiment of the present invention, a manufacturing method, including disposing one or more electrodes over an external surface of a membrane of an expandable balloon for insertion into an organ of a patient. a respective conductive coil is wound around a perimeter of each electrode, wherein the conductive coil is configured as a magnetic sensor.

The present invention will be more fully understood from the following detailed description of the embodiments thereof, taken together with the drawings in which:

DETAILED DESCRIPTION OF EMBODIMENTS

Overview

Figure 1:
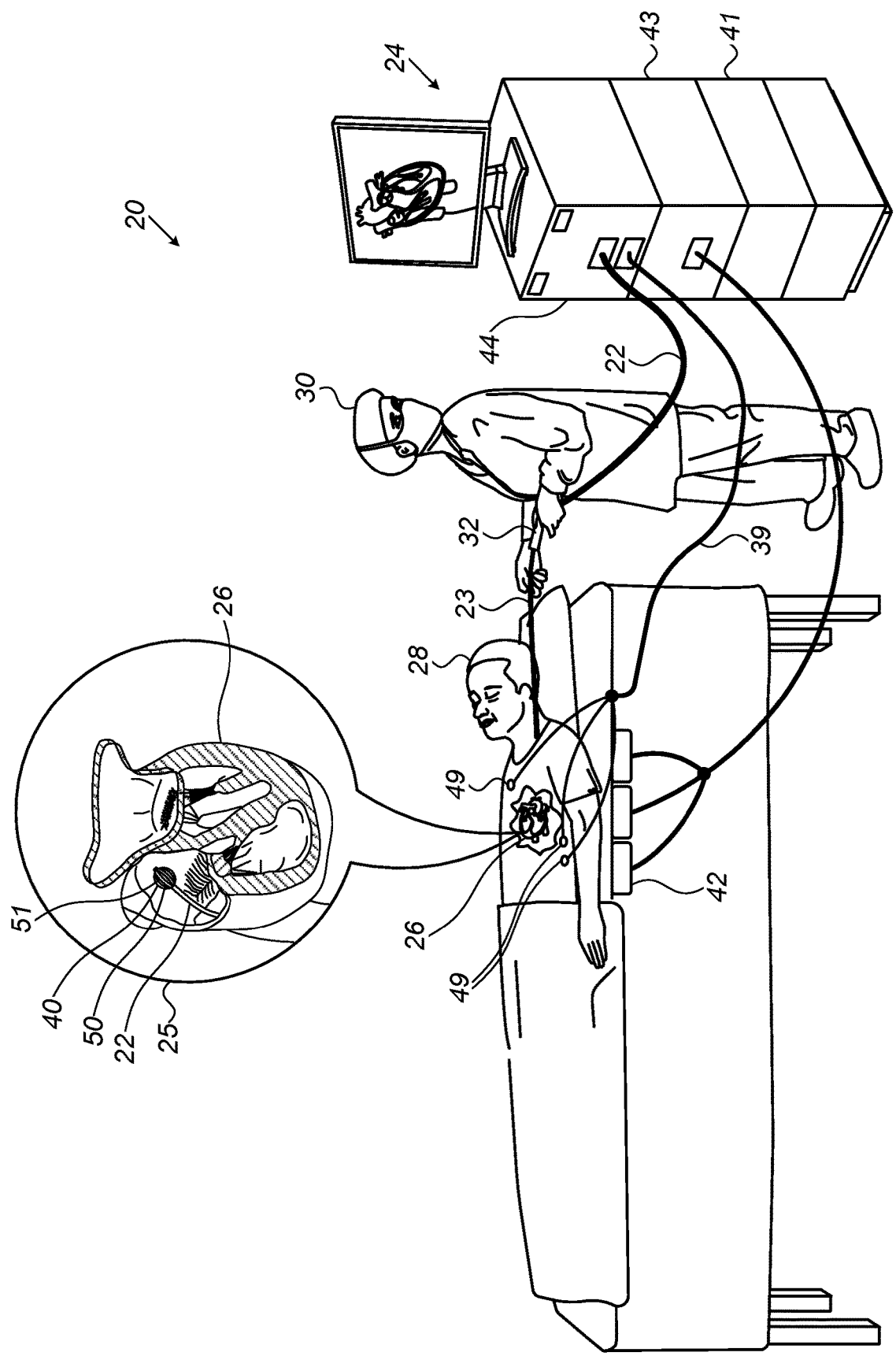
FIG. 1 is a schematic pictorial illustration of a catheter-based position tracking and ablation system comprising a balloon catheter, in accordance with an embodiment of the present invention.

A balloon catheter typically comprises an expandable balloon that is coupled to a distal end of a shaft for insertion into a cavity of an organ of a patient. For the best outcome of a balloon treatment, a physician may need to determine an exact location, orientation and shape of the balloon inside the organ. For example, in a balloon ablation procedure performed inside the left atrium of the heart, the physician may need to know the exact location and orientation of the balloon relative to an opening of a pulmonary vein so as to evenly ablate tissue over an entire circumference of the opening.

In the context of this disclosure, the term "balloon location and orientation" refers to either or both of (i) a location plus direction in space of the longitudinal axis defined by a distal end of the shaft, and (ii) a location plus tilt or deflection of the balloon relative to the longitudinal axis. When the expanded balloon is free of constraints the surface of the balloon revolves around a direction parallel to the longitudinal axis. In such case, ablation elements, such as electrodes, which lay on an equator of the balloon (the equator defining a plane perpendicular to the direction of the balloon) are aligned perpendicular to the longitudinal axis.

However, when the balloon is constrained and/or deflected upon contact with cavity wall tissue, the balloon direction is not necessarily parallel to the longitudinal axis. As a result, the ablation electrodes are tilted at some unknown angle. For example, the electrodes may be tilted relative to an opening of the pulmonary vein to be ablated by the electrodes, resulting in uneven ablation.

Embodiments of the present invention that are described hereinafter provide an expandable radiofrequency balloon catheter comprising one or more magnetic sensors, such as single-axis magnetic sensors, each of embodied as a conductive coil wound around a respective electrode disposed over an external surface of the expandable membrane of the balloon. In some embodiments, the electrode is an RF ablation electrode. Using the disclosed sensors, a processor of a magnetic tracking system estimates a spatial configuration of the balloon inside the organ, comprising a location and/or orientation and/or shape of the balloon, accurately enough in demanding clinical applications, as described below.

Additionally or alternatively, the processor may be configured to estimate at least one of a deflection of the balloon relative to a longitudinal axis defined by the distal end of the shaft and a roll angle (i.e., rotation angle) about the longitudinal axis. These parameters are also considered examples of the "spatial configuration" of the balloon. In this way, the physician can advance the balloon to target tissue otherwise difficult to access, and only then expand the balloon. After the balloon is fully expanded, the magnetic position system, using the disclosed coils, is capable of tracking the balloon location and/or direction even if the balloon is constrained and/or deflected relative to a longitudinal axis defined by a distal end of a shaft.

In some embodiments, the spatial configuration of the expandable balloon further comprises a shape of the balloon inside the organ. The processor may estimate the shape, for example, by identifying an extent of expansion of the balloon. In an embodiment, the processor is configured to estimate the shape by detecting whether the balloon is fully expanded or not. In some embodiments, using the disclosed coil sensors the physician can determine the balloon orientation even when the balloon is only partially expanded (e.g. partially inflated).

Typically, with multiple RF ablation electrodes disposed over the membrane, multiple respective magnetic sensors can be disposed over an entire circumference of the expandable balloon. In some embodiments, the disclosed coil encompasses an area approximately equal to that of the ablation electrode, which is sufficient, for a coil with several windings around the electrode perimeter, to generate a location signal. Typically, each winding width is several tens of microns, so that the overall width of the perimeter is kept below half a millimeter.

In some embodiments, a single lead is used to electrically connect both the ablation electrode and the wound coil to respective interfaces of the system (i.e., a single lead, which is configured to provide a common electrical contact to an RF ablation electrode and the coil wound around the RF ablation electrode), so only one additional lead is required for the coil (i.e., to close a circuit by connecting the other end of the coil). In some embodiments, the ablation electrode is separated into two or more sub-electrodes, and both of the leads to the ablation electrode are used to connect to the coil, so that no extra leads are required.

Typically, the processor is programmed in software containing a particular algorithm that enables the processor to conduct each of the processor-related steps and functions outlined hereinafter.

The ability to estimate the shape of the balloon is enabled, for example, by the fact that the coils (the position sensors) are fitted on the membrane, away from the longitudinal axis of the catheter. By providing magnetic tracking capabilities of balloon position, orientation and shape as described above, embodiments of the present invention enable a physician operating the balloon catheter to align the balloon inside a cavity relative to target tissue, so as for example, to uniformly ablate tissue.

Furthermore, the disclosed coils may eliminate the need to incorporate additional means for tracking the balloon catheter position and orientation. For example, the disclosed technique may enable providing a "smooth" balloon, by eliminating the need to fit an additional position and/or orientation sensing element at a protruding distal edge of the balloon catheter.

System Description

FIG. 1 is a schematic pictorial illustration of a catheter-based position tracking and ablation system 20 comprising a balloon catheter 40, in accordance with an embodiment of the present invention. System 20 is used to determine the position and direction of balloon catheter 40, seen in an inset 25 coupled to a distal end of a shaft 22. System 20 is further used for providing information regarding the balloon state of inflation (e.g., if balloon 40 is fully expanded). Typically, balloon catheter 40 is used for therapeutic treatment, such as spatially ablating cardiac tissue, for example at the left atrium.

Physician 30 navigates balloon catheter 40 to a target location in a heart 26 of a patient 28 by manipulating shaft 22 using a manipulator 32 near the proximal end of the catheter and/or deflection from a sheath 23. Balloon catheter 40 is inserted, in a folded configuration, through sheath 23, and only after the balloon is retracted from the sheath 23 does balloon catheter 40 regain its intended functional shape. By containing balloon catheter 40 in a folded configuration, sheath 23 also serves to minimize vascular trauma on its way to the target location.

For position and direction measurements, balloon catheter 40 incorporates conductive coils 50, which are disposed on an outer surface of the balloon membrane 44 and are used as magnetic position sensors, as described below. Each coil is wound around a perimeter of a radiofrequency (RF) ablation electrode 51, where the ablation electrode and the coil share an electrical lead, and are both connected by wires running through shaft 22 to interface circuits 44 in a console 24. A detailed view of coil 50 wound around the perimeter of ablation electrode 51, where both are disposed over membrane 44, is shown in inset 35 of FIG. 2.

Console 24 comprises a processor 41, typically a general-purpose computer and a suitable front end and interface circuits 44 for transmitting and receiving signals, such as RF signals and position signals, respectively. Interface circuits 44 may receive electrocardiograms from surface electrodes 49, which are seen in the exemplified system as attached by wires running through a cable 39 to the chest and to the back of patient 28.

Console 24 comprises a magnetic-sensing sub-system. Patient 28 is placed in a magnetic field generated by a pad containing magnetic field radiators 42, which are driven by unit 43. The magnetic fields irradiated by radiators 42 generate signals in coils 50, which are then provided as corresponding electrical inputs to processor 41, which uses the generated signals to calculate a position and/or direction of balloon catheter 40.

The method of position sensing using external magnetic fields is implemented in various medical applications, for example, in the CARTO™ system, produced by Biosense Webster Inc., and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

Processor 41 is typically programmed in a suitable software code to carry out the functions described herein. The software may be downloaded to the computer in electronic form, over a network, for example, or it may, alternatively or additionally, be provided and/or stored on non-transitory tangible media, such as magnetic, optical, or electronic memory. In particular, processor 41 runs a dedicated algorithm as disclosed herein, including in FIG. 4, that enables processor 41 to perform the disclosed steps, as further described below.

FIG. 1 shows only elements related to the disclosed techniques, for the sake of simplicity and clarity. System 20 typically comprises additional modules and elements that are not directly related to the disclosed techniques, and thus are intentionally omitted from FIG. 1 and from the corresponding description.

Configuring Perimeter of Balloon Electrode as Location Sensor

Figure 2:
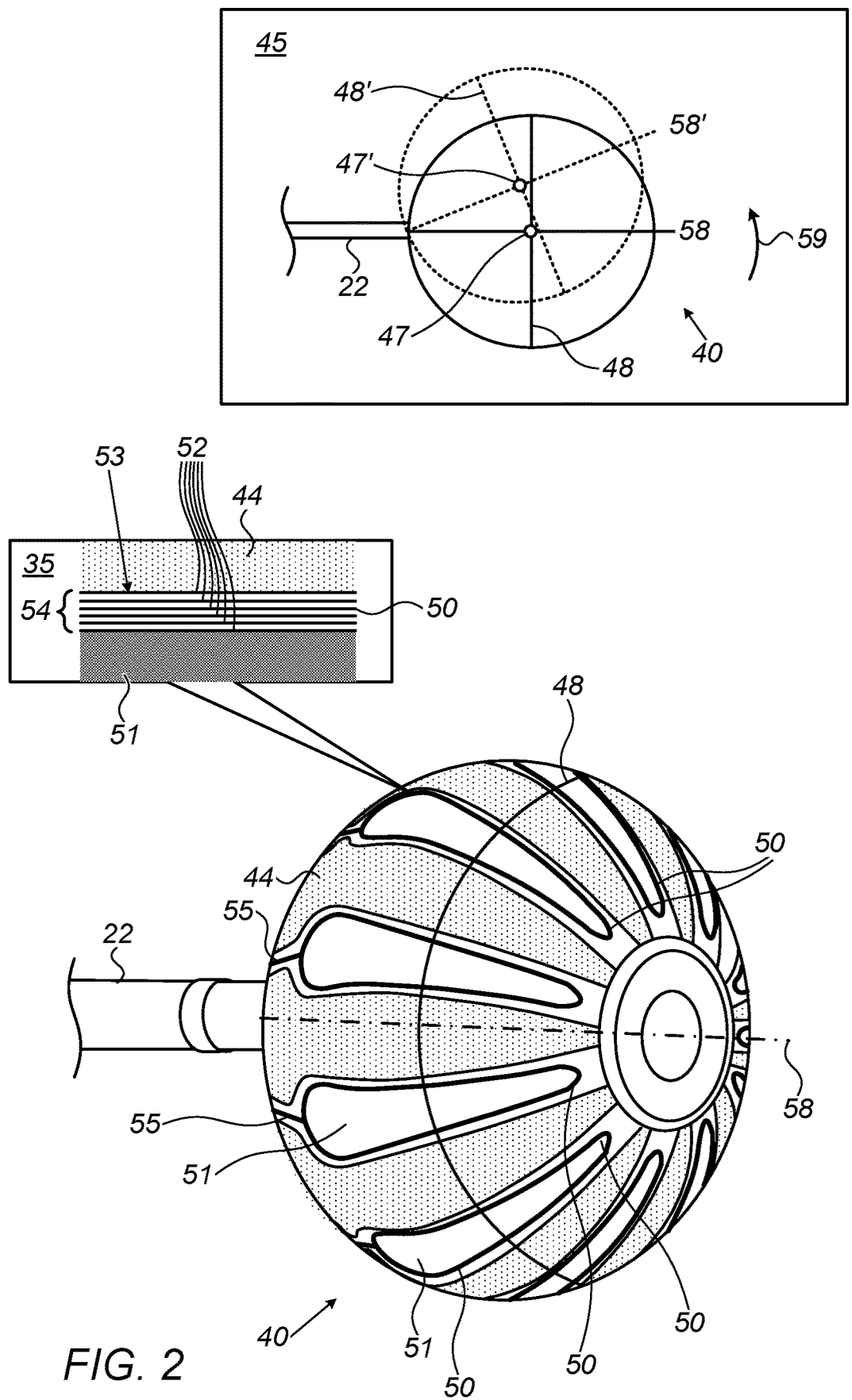
FIG. 2 is a schematic pictorial illustration of the balloon catheter of FIG. 1 comprising one or more coil sensors, in accordance with an embodiment of the present invention.

FIG. 2 is a schematic pictorial illustration of balloon catheter 40 of FIG. 1 comprising one or more coil sensors 50, in accordance with an embodiment of the present invention. As seen, balloon 40 is coupled to the distal end of shaft 22 that defines a longitudinal axis 58. Balloon catheter 40 comprises RF ablation electrodes 51 that are evenly disposed over an equator 48 of expandable membrane 44. Each coil 50 is wound around the perimeter of each RF ablation electrode 51. As further seen, balloon catheter 40 is free of constraints, and thus equator 48 lies in a plane perpendicular to longitudinal axis 58.

In an embodiment, coil 50 is disposed on a flexible printed circuit board (PCB) 53, and flexible PCB 53 is attached to expandable membrane 44. In some embodiments coil 50 is made of a wire wound and encapsulated over to the flexible PCB. In another embodiment, coil 50 is patterned (e.g., printed) over flexible PCB 53.

Inset 45 shows balloon catheter 40 in two directions, the "free" direction parallel to axis 58, and a "deflected" direction 58'. As seen, when the balloon is deflected, for example, due to contact with wall tissue, the center location of the balloon changes from a location 47 to a deflected location 47'. Moreover, equator 48 is deflected to an equator 48', which means that electrodes 51 are aligned around the new direction 58'. Location 47' and direction 58' can be tracked using the disclosed coil sensors disposed over membrane 44, as described below. In some embodiments, based on signals from the coil sensors, processor 41 estimates a roll angle 59 of balloon catheter 40 around axis 58.

FIG. 2 shows that each RF ablation electrode 51 and a respective coil 50 share a lead 55, as further described below. In an embodiment, shown in inset 35, each coil 50 is made of several turns 52 (i.e., windings 52). Each turn 52 of coil 50 has a width of several tens of microns, so that the overall width 54 of the perimeter (i.e., of coil 50) is kept to no more of several hundred microns. Each ablation electrode has an area of several tens of mm2, so that a coil wound several turns around the electrode perimeter has an effective area of several hundred mm2, which is sufficient for generating the required signal. A typical width of a turn on coil 50 is about 40-50 microns, so six or seven turns results in an effective area of about 250-350 mm2.

The illustration shown in FIG. 2 is chosen purely for the sake of conceptual clarity. Other geometries of ablation electrodes are possible. Elements which are not relevant to the disclosed embodiments of the invention, such as irrigation ports and temperature sensors, are omitted for the sake of clarity.

Figure 3:
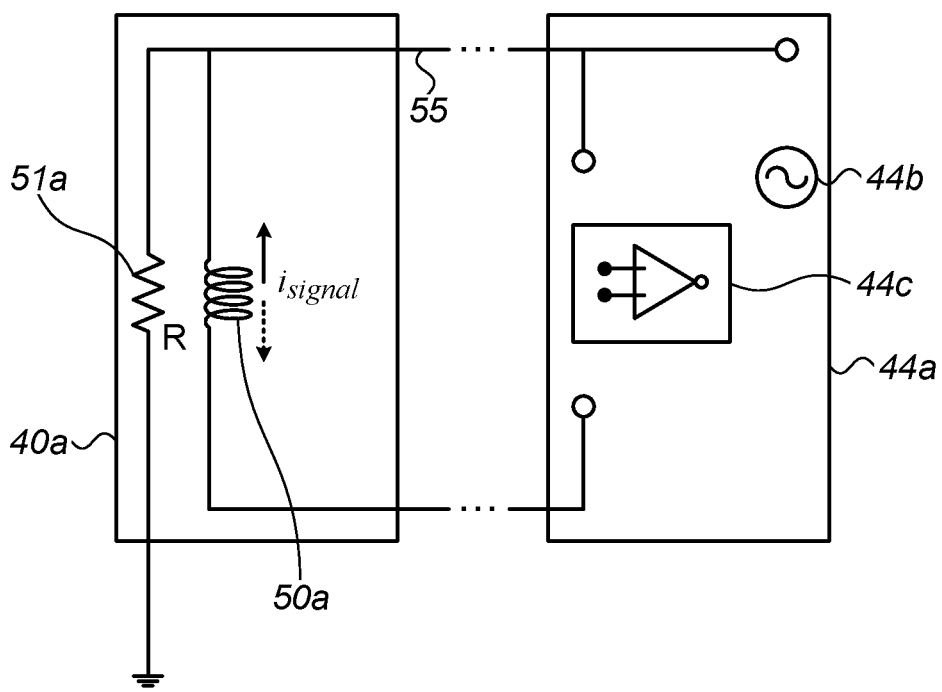
FIG. 3 is a schematic diagram of an electrical connection scheme of the ablation electrode and the coil sensor of FIG. 2, in accordance with an embodiment of the present invention.

FIG. 3 is a schematic diagram of an electrical connection scheme of RF ablation electrode 51 and coil sensor 50 of FIG. 2, in accordance with an embodiment of the present invention. The content of frame 40a schematically shows the disclosed electrical circuit formed with each ablation electrode 51 (represented by a resistor 51a), and the wound coil 50 (represented by a coil 50a). As seen, coil 50a shares a lead 55 with resistor 51a, wherein coil 50a generates a tracking signal $i_{Signal}$.

Signals generated by coil 50a are transmitted using lead 55 and subsequently by a wire in shaft 22 (not shown) to electrical readout circuitry 44c included in interface circuits 44 inside console 24, schematically shown by a frame 44a. An RF source 43c to electrode 51a is also seen inside frame 44a. Using a single lead 55 to connect both coil 50a and resistor 51a (i.e., RF ablation electrode 51) to interface circuits 44 saves separate dedicated wiring.

The schematic diagram shown in FIG. 3 is chosen purely for the sake of conceptual clarity. Other connection schemes that utilize a shared lead, such as a lead shared as a common electrical ground, are possible. In an embodiment, coil 50 may be connected via a reinforced isolated amplifier that converts the generated signal from a high-voltage domain to a low-voltage domain. Additional elements may be used as well, such as electronic demodulation circuits.

Figure 4:
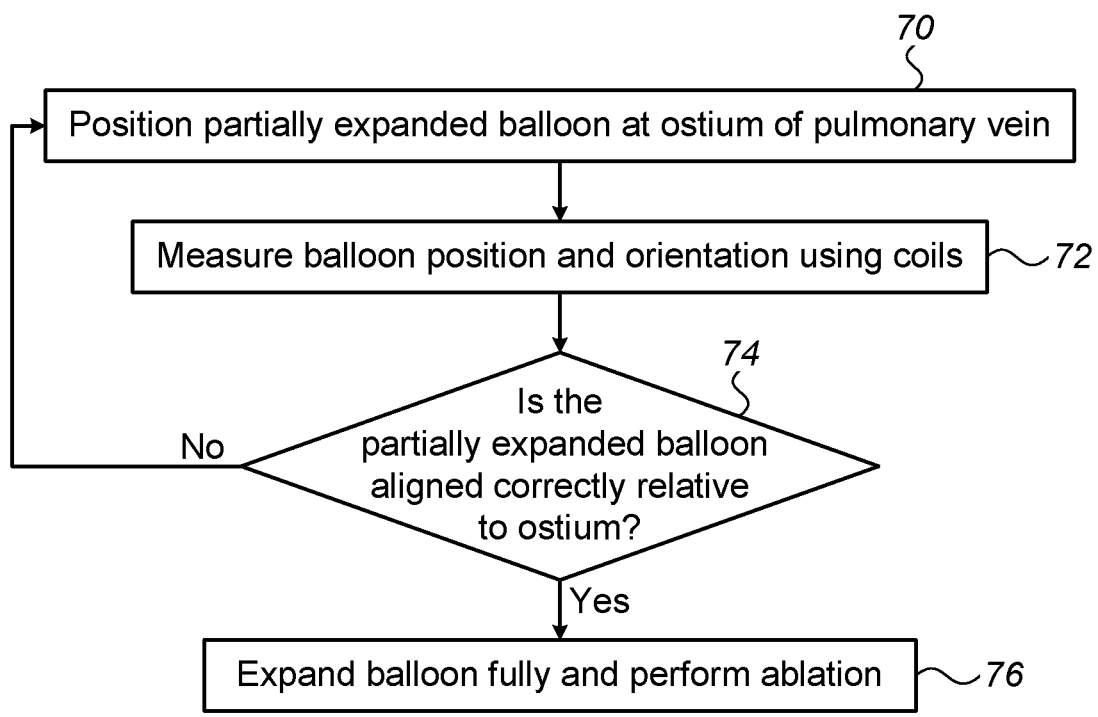
FIG. 4 is a flow chart that schematically illustrates a method and algorithm for tracking the expandable balloon of FIG. 2 using one or more coil sensors, in accordance with an embodiment of the present invention.

FIG. 4 is a flow chart that schematically illustrates a method and algorithm for tracking the expandable balloon of FIG. 2 using one or more coil sensors, in accordance with an embodiment of the present invention. The algorithm of FIG. 4 ensures that one skilled in the computer art can generate the necessary software code, as well as any other needed auxiliary steps, for a general-purpose computer to carry out the specific purposes of tracking the location or shapes of the expandable balloon of FIG. 2. The algorithm according to the present embodiment carries out a process that begins with physician 30 positioning a partially expanded balloon catheter 40 at a target location inside a cardiac cavity of heart 26, such as at an ostium of a pulmonary vein, at a balloon positioning step 70. Next, at a balloon tracking step 72, system 20 uses coils 50 to measure a position and an orientation of balloon catheter 40, e.g., relative to a given cross section (i.e., slice) of the ostium. Next, physician 30 decides if the partially expanded balloon catheter 40 is aligned correctly relative to the ostium, at a decision step 74.

If physician 30 finds that balloon catheter 40 is well aligned, then physician 30 fully inflates the balloon and performs a treatment, such as an RF ablation, in an RF balloon treatment step 76.

Figure 5:
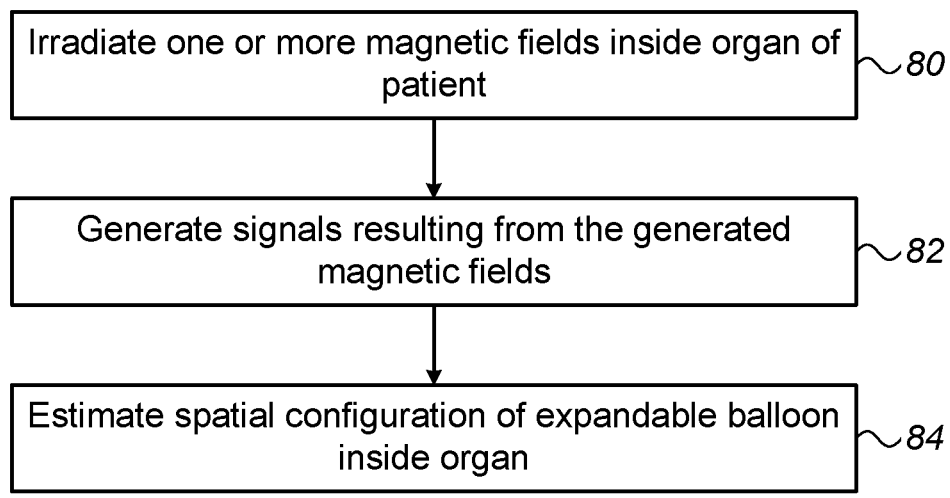
FIG. 5 is a flow chart that schematically illustrates a method and algorithm for estimating a spatial configuration of the expandable balloon of FIG. 2, in accordance with an embodiment of the present invention.

FIG. 5 is a flow chart that schematically illustrates a method and algorithm for estimating a spatial configuration of the expandable balloon of FIG. 2, in accordance with an embodiment of the present invention. By virtue of the embodiments described herein, we have devised an algorithm, as shown in FIG. 5, for determining locations as well as other operational parameters of a balloon catheter while the balloon is located within biological tissues. In particular, the method can be achieved with the following algorithm exemplified in FIG. 5: irradiating (80) one or more magnetic fields inside an organ of a patient, and generating (82) signals resulting from the generated magnetic fields. The signals are generated by one or more conductive coils from the magnetic fields irradiating upon the coils, each of which is disposed proximate each electrode disposed over an external surface of a membrane of an expandable balloon coupled to a distal end of a shaft inserted in an organ of the patient. The step continues with using a magnetic tracking system, based on the generated signals and estimating (84) a spatial configuration of the expandable balloon inside the organ. It is noted that the estimating may include estimating one or more of the following: estimating the location of the balloon inside the organ, estimating the orientation of the balloon inside the organ, estimating at least one of a deflection of the balloon relative to a longitudinal axis defined by the distal end of the shaft and a roll angle about the longitudinal axis, and estimating a shape of the balloon inside the organ. The step of estimating a shape may include identifying an extent of expansion of the balloon or detecting whether the balloon is fully expanded or not.

The example flow chart shown in FIG. 4 is chosen purely for the sake of conceptual clarity. The present embodiment also comprises additional steps of the algorithm, such as acquiring intra-cardiac electrocardiograms, which have been omitted from the disclosure herein purposely in order to provide a more simplified flow chart given that one skilled in this art has the requisite background knowledge for programming such algorithm in the field of electrophysiology. In addition, other steps, such as temperature measurements and applying irrigation, are omitted for clarity of presentation.

Although the embodiments described herein mainly address cardiac applications, the methods and systems described herein can also be used in other applications, such as in otolaryngology, neurology, cardiology, blood vessel treatment and renal denervation.

It will thus be appreciated that the embodiments described above are cited by way of example, and that the present invention is not limited to what has been particularly shown and described hereinabove. For example, cardiac signal sensing electrodes can be utilized in place of the ablation electrodes or a combination of both signal-sensing electrodes and ablation electrodes can be utilized. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An expandable balloon coupled to a distal end of a shaft for insertion into an organ of a patient, the expandable balloon comprising:
   (a) an expandable membrane;
   (b) one or more electrodes disposed over an external surface of the membrane; and
   (c) one or more respective conductive coils, each conductive coil wound several turns around an entirety of a perimeter of a respective electrode, the one or more conductive coils are being configured as magnetic sensors.

2. The expandable balloon according to claim 1, and further comprising one or more respective leads, each configured to provide a common electrical contact for an electrode and for a coil wound around a perimeter of the electrode.

3. The expandable balloon according to claim 1, the conductive coil is being disposed on a flexible printed board (PBC), and the flexible PCB is being attached to the expandable membrane.

4. The expandable balloon according to claim 1, the one or more electrodes are being radiofrequency (RF) ablation electrodes.

5. The expandable balloon according to claim 1, the one or more electrodes is being selected from a group of electrodes consisting of ablation electrodes, sensing electrodes or combinations thereof.

6. A system, comprising:
(a) an expandable balloon coupled to a distal end of a shaft for insertion into an organ of a patient, the expandable balloon comprising:
(i) an expandable membrane;
(ii) one or more electrodes disposed over an external surface of the membrane; and
(iii) one or more respective conductive coils, each conductive coil wound several turns around a perimeter of a respective electrode such that each conductive coil encircles the respective electrode, the one or more conductive coils being configured as magnetic sensors; and
(b) a processor, which is configured to, based on signals received from the one or more conductive coils, estimate a spatial configuration of the expandable balloon inside the organ.

7. The system according to claim 6, the expandable balloon further comprising one or more respective leads, each configured to provide a common electrical contact for an electrode and for the conductive coil wound around a perimeter of the electrode.

8. The system according to claim 6, the conductive coil is being disposed on a flexible printed board (PBC), and the flexible PCB being attached to the expandable membrane.

9. The system according to claim 6, the processor is being configured to estimate the spatial configuration of the expandable balloon by estimating a location of the balloon inside the organ.

10. The system according to claim 6, the processor is being configured to estimate the spatial configuration of the expandable balloon by estimating an orientation of the balloon inside the organ.

11. The system according to claim 6, the processor is being configured to estimate the orientation by estimating at least one of a deflection of the balloon relative to a longitudinal axis defined by the distal end of the shaft and a roll angle about the longitudinal axis.

12. The system according to claim 6, the processor is being configured to estimate the spatial configuration of the expandable balloon by estimating a shape of the balloon inside the organ.

13. The system according to claim 12, the processor is being configured to estimate the shape by identifying an extent of expansion of the balloon.

14. The system according to claim 12, the processor is being configured to estimate the shape by detecting whether the balloon is fully expanded or not.

15. A catheter for electrophysiology applications, comprising:
(a) a shaft having a distal end; and
(b) an end effector coupled to the distal end of the shaft, the end effector including:
(i) an expandable membrane having an outer surface,
(ii) an electrode secured to the outer surface of the membrane, and
(iii) a position sensor secured to the outer surface of the membrane, the position sensor including a coil having a plurality of windings extending around an entire perimeter of the electrode.

16. The catheter of claim 15, the end effector further comprising an electrical lead electrically coupled to each of the electrode and the position sensor.

17. The catheter of claim 16, the electrode including an ablation electrode.

18. The catheter of claim 16, further comprising a wire electrically coupled to the electrical lead, the wire extending along the shaft.

19. A system comprising:
(a) the catheter of claim 18; and
(b) a processor electrically coupled to the wire, the wire and the electrical lead being configured to transmit signals generated by the position sensor to the processor.

20. An end effector of a catheter, the end effector comprising:
(a) an expandable membrane having an outer surface;
(b) an electrode secured to the outer surface of the membrane; and
(c) a position sensor secured to the outer surface of the membrane, the position sensor including a coil having a plurality of windings extending around a perimeter of the electrode such that the coil surrounds the electrode.

21. The end effector of claim 20, further comprising an electrical lead electrically coupled to each of the electrode and the position sensor.

22. The end effector of claim 21, the electrode including an ablation electrode.

23. A system comprising:
(a) the end effector of claim 22; and
(b) a processor electrically coupled to the electrical lead via a wire, the wire and the electrical lead being configured to transmit signals generated by the position sensor to the processor.

* * * * *

UNITED STATES PATENT AND TRADEMARK OFFICE
CERTIFICATE OF CORRECTION

PATENT NO. : 11,751,936 B2
APPLICATION NO. : 16/198487
DATED : September 12, 2023
INVENTOR(S) : Meir Bar-Tal It is certified that error appears in the above-identified patent and that said Letters Patent is hereby corrected as shown below:

On the Title Page

Item [56], Column 2, Line 2, delete "PCT/IBZ019/059657" and insert -- PCT/IB2019/059657 --.

In the Claims

In Column 8, Line 54, in Claim 1, after "coils" delete "are".

In Column 8, Line 56, in Claim 2, after "claim 1," delete "and".

In Column 8, Line 62, in Claim 3, after "coil" delete "is".

In Column 8, Line 63, in Claim 3, delete "(PBC)" and insert -- (PCB) --.

In Column 8, Line 63, in Claim 3, after "flexible PCB" delete "is".

In Column 8, Line 66, in Claim 4, after "electrodes" delete "are".

In Column 9, Line 2, in Claim 5, after "electrodes" delete "is".

In Column 9, Line 28, in Claim 8, after "coil" delete "is".

In Column 9, Line 29, in Claim 8, delete "(PBC)" and insert -- (PCB) --.

In Column 9, Line 31, in Claim 9, after "processor" delete "is".

In Column 9, Line 34, in Claim 10, after "processor" delete "is".

In Column 9, Line 38, in Claim 11, after "processor" delete "is".

Signed and Sealed this
Twenty-sixth Day of December, 2023

Katherine Kelly Vidal
*Director of the United States Patent and Trademark Office*

In Column 9, Line 44, in Claim 12, after "processor" delete "is".

In Column 9, Line 48, in Claim 13, after "processor" delete "is".

In Column 10, Line 1, in Claim 14, after "processor" delete "is".